United States Patent [19]

Hoult

[11] Patent Number: 6,121,052
[45] Date of Patent: *Sep. 19, 2000

[54] REFLECTANCE SAMPLER AND METHOD OF USE

[75] Inventor: Robert A. Hoult, Beaconsfield, United Kingdom

[73] Assignee: PerkinElmer International C.V., Switzerland

[*] Notice: This patent issued on a continued prosecution application filed under 37 CFR 1.53(d), and is subject to the twenty year patent term provisions of 35 U.S.C. 154(a)(2).

[21] Appl. No.: 08/881,402

[22] Filed: Jun. 24, 1997

[30] Foreign Application Priority Data

Jun. 27, 1996 [GB] United Kingdom ................... 9613499

[51] Int. Cl.[7] .............................. G01N 21/01; G01N 1/00
[52] U.S. Cl. ......................... 436/165; 356/244; 422/102; 436/164; 436/174
[58] Field of Search ............................ 422/55, 58, 82.05, 422/82.09, 99, 102, 104; 436/164, 174, 165; 435/288.4, 305.2, 305.3, 305.4; 356/244

[56] References Cited

U.S. PATENT DOCUMENTS

| 3,572,892 | 3/1971 | Metzger et al. ................... 356/244 X |
|---|---|---|
| 3,728,228 | 4/1973 | Duranty ................................. 435/288.3 |
| 3,745,091 | 7/1973 | McCormick .......................... 435/305.3 |
| 4,299,920 | 11/1981 | Peters .................................... 435/288.4 |
| 4,728,607 | 3/1988 | Dorn et al. ........................... 435/288.4 |
| 4,741,619 | 5/1988 | Humphries et al. ................ 422/102 X |
| 5,095,213 | 3/1992 | Strongin .............................. 356/244 X |
| 5,290,705 | 3/1994 | Davis ...................................... 436/164 |
| 5,453,252 | 9/1995 | Truett .................................. 422/102 X |
| 5,792,653 | 8/1998 | Weibezahn et al. ................. 435/288.5 |

FOREIGN PATENT DOCUMENTS

| 2522014 | 8/1983 | France . |
|---|---|---|
| 4132379 | 4/1993 | Germany ............................ 435/305.2 |
| 11-144970 | 6/1989 | Japan ................................... 435/305.2 |
| 9501559 | 1/1995 | WIPO . |

OTHER PUBLICATIONS

M. Jansson et al. *J. Chromatogr.* 1992, 626, 310–314.

*Primary Examiner*—Arlen Soderquist
*Attorney, Agent, or Firm*—St. Onge Steward Johnston & Reens LLC

[57] ABSTRACT

A carrier for use in the preparation of samples for spectroscopic analysis comprises a generally planar body 10 the upper surface of which is formed with ridges or walls 14 which define compartments 15 into material to be analysed is spread. The surface of the compartments is preferably coated with a reflecting material such as aluminium. This form of carrier greatly facilitates the production of a layer of uniform thickness.

6 Claims, 1 Drawing Sheet

REFLECTANCE SAMPLER AND METHOD OF USE

TECHNICAL FIELD

This invention relates to the preparation of samples for spectroscopy and in particular relates to the preparation of samples which have a paste or paste-like consistency. The term "paste" or "paste-like" is intended to include materials which have a relatively viscous character ranging from a material such as chocolate which is almost solid but can be spread, to a thin slurry-type material comprising powder mixed in a liquid. All these materials can be formed, e.g. by spreading into a thin layer for spectroscopic analysis. The analysis is usually carried out using radiation in the infra-red (IR) range of wavelengths.

BACKGROUND ART

It has proved difficult in the past to obtain properly representative spectra of paste or paste-like materials, because of problems in forming a uniformly thin film of the paste. In one known technique a thin film is pressed out between a pair of crystal plates and analysed in transmission. This technique has inherently low penetration depth which gives problems with fundamentally inhomogeneous samples. Also the crystal plates which have to be suitable for use with infra-red spectroscopy are expensive and thus have to be cleaned after each measurement for re-use.

Another known technique is described in U.S. Pat. No. 5,453,252. This makes use of a mesh which defines a plurality of pores. The sample to be analysed is held in the pores by surface tension effects. The technique relies on analysis in transmission and does not produce a film having a reliably uniform thickness.

SUMMARY OF THE INVENTION

The present invention aims to alleviate the above disadvantages.

According to one aspect of the present invention there is provided a carrier or substrate for use in the preparation of samples for spectroscopic analysis, said carrier comprising an upper surface which is formed with shallow ridges or walls, which define one or more compartments into which paste or paste-like material can be spread.

The carrier should be made from a material which reflects the radiation used to spectroscopically investigate the sample. The height of the ridges should correspond to the desired thickness of the layer to be investigated. Typically this will be of the order of 10 microns for IR analysis. A typical spacing between adjacent ridges will be 100 microns.

To form a layer some paste-like material is placed on the carrier and then spread using a suitable scraper with a straight edge. The action of the scraper moving over the upper surface of the ridges automatically produces a layer of a uniform thickness equal to the ridge height.

The carrier has the advantage that it is simple and inexpensive to produce. One way of producing the carrier is to form a negative of the carrier surface in the surface of a metal plate, e.g. a brass plate. This plate will thus be formed with a series of grooves at positions corresponding to the ridges required in the carrier.

Suitable plastics material is then pressed against the metal surface to thereby form the carrier surface defined above. It is envisaged the carrier will be produced in large quantities by injection moulding, thereby reducing the unit costs.

It is believed that the exact shape of ridges is not critical. The ridge can be of an inverted V-shape, which may be the preferable shape since it has a small cross-section for specular reflection in the principal direction. However, a round top ridge is also possible and may perform equally well. It is possible to provide a single set of ridges running in one direction.

An alternative arrangement is an intersecting pattern, thereby providing an array of compartments into which the paste-like material can be spread. The ridges defining the intersecting pattern may be arranged orthogonally, although it is also possible that they could be arranged to extend at angles other than 90°.

BRIEF DESCRIPTION OF THE DRAWINGS

The invention will be described now by way of example only, with particular reference to the accompanying drawings. In the drawings.

DETAILED DESCRIPTION OF THE PREFERRED EMBODIMENT

Figure 1:
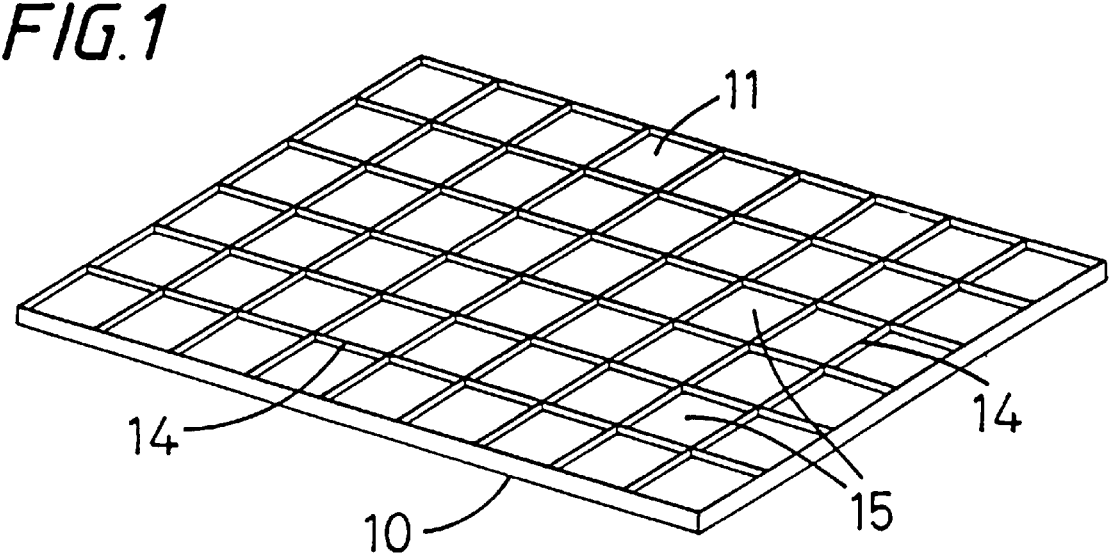
FIG. 1 is a perspective view of a carrier in accordance with the present invention.
Figure 2:
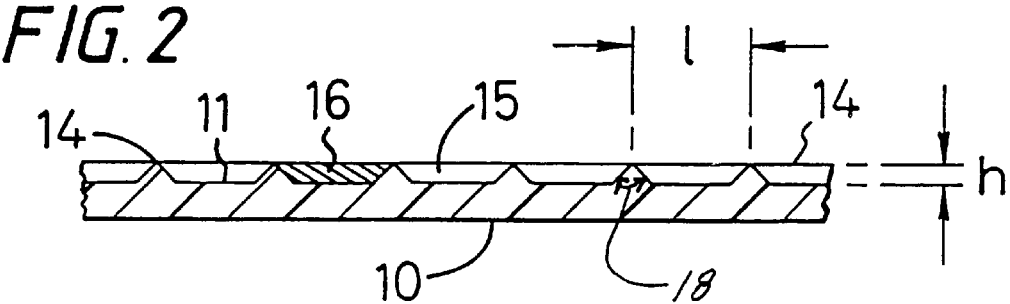
FIG. 2 is a sectional view of part of the carrier.

The carrier 10 is formed from a suitable plastics material such as polystyrene and has an upper surface 11, which can reflect radiation which is used to investigate samples. The surface 11 may comprise a layer of aluminium coated on the polystyrene. The upper surface is formed with intersecting ridges or walls 14 which define an array of compartments 15 into which material to be analysed is spread. As shown in FIG. 2 each ridge in this example is an inverted V-shape. The apex angle 18 of the ridge in this embodiment is 90 degrees. The height (L) of each ridge is approximately 10 $\mu$ and the spacing (L) between ridges is approximately 100 $\mu$. Material 16 is spread into the compartments 15 using a spreader with a straight edge which rides along the upper edges of the ridges. This produces a thin film of material having a uniform thickness of approximately 10 $\mu$. When the material 16 is analysed the carrier is placed into an IR spectrometer and analysing radiation incident on the material passes through the material 16 and is reflected back from the surface (11) of each compartment 15 to a detecting device of the spectrometer.

In the example given above the height of each ridge is approximately 10 $\mu$. Other heights can be used and it is envisaged that said heights will lie in the range of approximately 5 $\mu$ to 100 $\mu$.

The carrier can be produced by injection moulding the plastic material and then forming a layer of aluminium on the ridged surface 11 by an evaporation process.

The present carrier is simple and inexpensive to produce and is easily disposable.

As described above the compartments are defined by intersecting ridges 14. It is possible to provide an arrangement in which there is a single set of generally parallel ridges defining parallel extending compartments.

What is claimed is:

1. A method of forming a layer of a sample for spectrographic analysis comprising placing said sample on a carrier or substrate, said carrier or substrate comprising a surface which reflects the radiation used for spectroscopic analysis which is formed with a first set of parallel ridges or walls and a second set of parallel ridges or walls which intersect at an angle to define one or more compartments into which material can be spread, said method further comprising spreading said sample over said surface of said carrier to produce a layer of said sample having a thickness corresponding to the height of said ridges or walls.

2. The method according to claim 1, wherein said first set of parallel ridges or walls and said second set of parallel ridges or walls intersect at right angles.

3. The method according to claim 1, wherein either of said first set of parallel ridges or walls or said second set of parallel ridges or walls has a cross-section of an inverted V-shape.

4. The method according to claim 3, wherein the apex angle of either of said first set of parallel ridges or walls or said second set of parallel ridges or walls is approximately 90 degrees.

5. The method according to claim 1, wherein either of said first set of parallel ridges or walls or said second set of parallel ridges or walls has a curved shape.

6. Method according to claim 1, wherein the height of said first set of parallel ridges or walls and said second set of parallel ridges or walls is in the range of about 5$\mu$ to about 100$\mu$.

* * * * *